(12) United States Patent
Kucklick

(10) Patent No.: US 10,786,301 B2
(45) Date of Patent: Sep. 29, 2020

(54) ARTHROSCOPIC SURGICAL TEMPERATURE CONTROL SYSTEM

(71) Applicant: Cannuflow, Inc., Campbell, CA (US)

(72) Inventor: Theodore R. Kucklick, Campbell, CA (US)

(73) Assignee: Cannuflow, Inc., Scotts Valley, CA (US)

( * ) Notice: Subject to any disclaimer, the term of this patent is extended or adjusted under 35 U.S.C. 154(b) by 0 days.

(21) Appl. No.: 16/660,637

(22) Filed: Oct. 22, 2019

(65) Prior Publication Data

US 2020/0046418 A1 Feb. 13, 2020

Related U.S. Application Data

(63) Continuation of application No. 14/508,818, filed on Oct. 7, 2014, now Pat. No. 10,448,993, which is a continuation of application No. 11/228,046, filed on Sep. 15, 2005, now Pat. No. 8,852,184.

(51) Int. Cl.
| | |
|---|---|
| *A61B 18/18* | (2006.01) |
| *A61B 18/14* | (2006.01) |
| *A61B 17/34* | (2006.01) |
| *A61B 17/00* | (2006.01) |
| *A61B 18/00* | (2006.01) |

(52) U.S. Cl.
CPC ...... *A61B 18/148* (2013.01); *A61B 17/00234* (2013.01); *A61B 17/3421* (2013.01); *A61B 2017/00084* (2013.01); *A61B 2017/00088* (2013.01); *A61B 2017/00092* (2013.01); *A61B 2017/00119* (2013.01); *A61B 2018/00011* (2013.01); *A61B 2018/00029* (2013.01); *A61B 2018/00666* (2013.01); *A61B 2018/00678* (2013.01); *A61B 2018/00791* (2013.01); *A61B 2018/00809* (2013.01); *A61B 2018/00821* (2013.01); *A61B 2218/002* (2013.01); *A61B 2218/007* (2013.01)

(58) Field of Classification Search
CPC ............ A61B 2018/00005; A61B 2018/00636
USPC ........................ 606/20–26, 31.32, 42, 45–50
See application file for complete search history.

(56) References Cited

U.S. PATENT DOCUMENTS

| | | | | |
|---|---|---|---|---|
| 7,387,625 B2 * | 6/2008 | Hovda | ............... | A61B 18/1482 606/32 |
| 2003/0208193 A1 * | 11/2003 | Van Wyk | ........... | A61B 18/1206 606/34 |

* cited by examiner

*Primary Examiner* — Alexandra L Newton
*Assistant Examiner* — Rynae Boler
(74) *Attorney, Agent, or Firm* — Crockett & Crockett, PC; K. David Crockett, Esq.; Susan L. Crockett, Esq.

(57) ABSTRACT

An arthroscopic surgical temperature control system and method able to monitor and control the temperature within a surgical site during arthroscopic ablation procedures in order to prevent tissue damage is provided.

7 Claims, 8 Drawing Sheets

ARTHROSCOPIC SURGICAL TEMPERATURE CONTROL SYSTEM

This application is a continuation of U.S. application Ser. No. 14/508,818, filed Oct. 7, 2014, now U.S. Pat. No. 10,448,993, which is a continuation of U.S. application Ser. No. 11/228,046, filed Sep. 15, 2005, now U.S. Pat. No. 8,852,184.

FIELD OF THE INVENTIONS

The inventions described below relate the field of arthroscopic surgical equipment and more specifically, to radio frequency ablation systems.

BACKGROUND OF THE INVENTIONS

During minimally invasive surgeries, surgical instruments such as ablation probes, trocars, cannulas, and optical medical devices, including endoscopes, cystoscopes, arthroscopes, laparoscopes, etc., are inserted through small incisions or portals in a patient's body or body cavity and manipulated to perform surgical procedures within the patient.

Minimally invasive surgical procedures are safer than open surgery and result in quicker patient recovery, shorter hospital stays, and lower health care costs. Accordingly, minimizing invasiveness continues to be of importance, and there is a continuing need for devices and methods that achieve this objective.

One area that has benefited from minimally invasive surgical techniques is arthroscopic surgery. Arthroscopic surgery such as shoulder surgery has evolved over the last several years from being an open surgical procedure to an arthroscopic surgical procedure. This evolution is the result of technological advances in equipment, instruments and implants.

Radio frequency ablation devices are often used during arthroscopic surgical procedures such as arthroscopic shoulder surgery. Radio frequency ablation is used, among other applications, to smooth the surface as well as to seal fissures in the cartilage found in joints, articular cartilage. The goal of such treatment is to provide mechanical stability while preventing the expansion of degenerative lesions within the cartilage matrix. Use of thermal energy on articular cartilage is not without risk. Exposure of mature cartilage cells, chondrocytes, to uncontrolled heat can cause cell death and alter the mechanical properties of its surrounding matrix.

Joints, such as shoulders and knees, have joint space with small amounts of fluid volume available within the surgical site. When radio frequency ablation probes are used in joints with small joint space, the surrounding fluid in the joint can quickly heat up as the fluid acts as a heat sink. Temperatures exceeding 113° C. in surrounding non-targeted tissue can have adverse effects on the surgical site, surrounding tissue and the patient. Temperatures above 113° F. can cause cartilage tissue death rapidly. Presently, fluid temperatures within arthroscopic surgical sites are not specifically monitored during surgery and steps are not taken to maintain the fluid temperatures at safe levels, such as levels between 97° F. and 108° F., within the surgical site during ablation. Systems and methods are needed to monitor and control the temperature within a surgical site during arthroscopic surgical procedures in order to prevent tissue damage.

SUMMARY

DETAILED DESCRIPTION OF THE INVENTIONS

Figure 1:
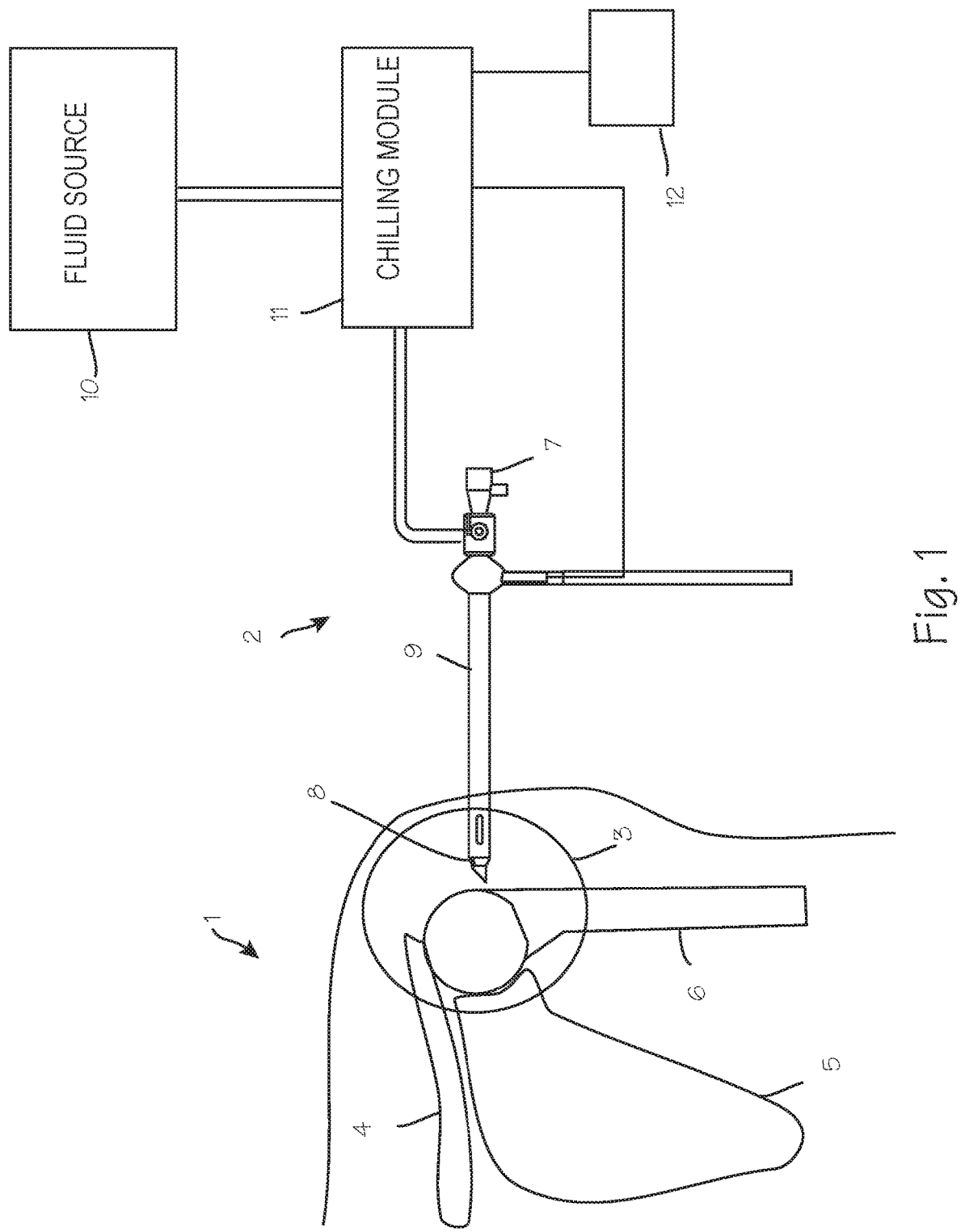
FIG. 1 illustrates a method of performing arthroscopic surgery on a patient using the temperature control system.

FIG. 1 illustrates a method of performing arthroscopic surgery on a patient's shoulder 1 using the temperature control system 2. The temperature control system 2 is shown inserted into a joint capsule 3 of a shoulder of a patient. Various anatomical landmarks are depicted including the patient's clavicle 4, scapula 5 and humerus 6. An arthroscopic instrument such as an arthroscope 7 is disposed within the temperature control system. The temperature control system 2 comprises a temperature sensor 8 operably coupled to an inflow/outflow sheath 9, a fluid source 10, a chilling module 11 in fluid communication with the fluid source and the inflow/outflow sheath 9 and a control system 12 in electrical communication with the temperature sensor 8 and the chilling module 11.

During arthroscopic shoulder surgery, the surgeon introduces the arthroscope into the shoulder via a first portal in order to visualize the surgical field. An ablation device is introduced through a second portal to smooth surfaces and seal fissures in articular cartilage. Optionally, an irrigating instrument may be introduced through a third portal in order to distend the joint, irrigate the surgical field and thereby maintain a clear view. As discussed below, a temperature control system may used to control fluid temperature in the surgical site of the shoulder.

Figure 2:
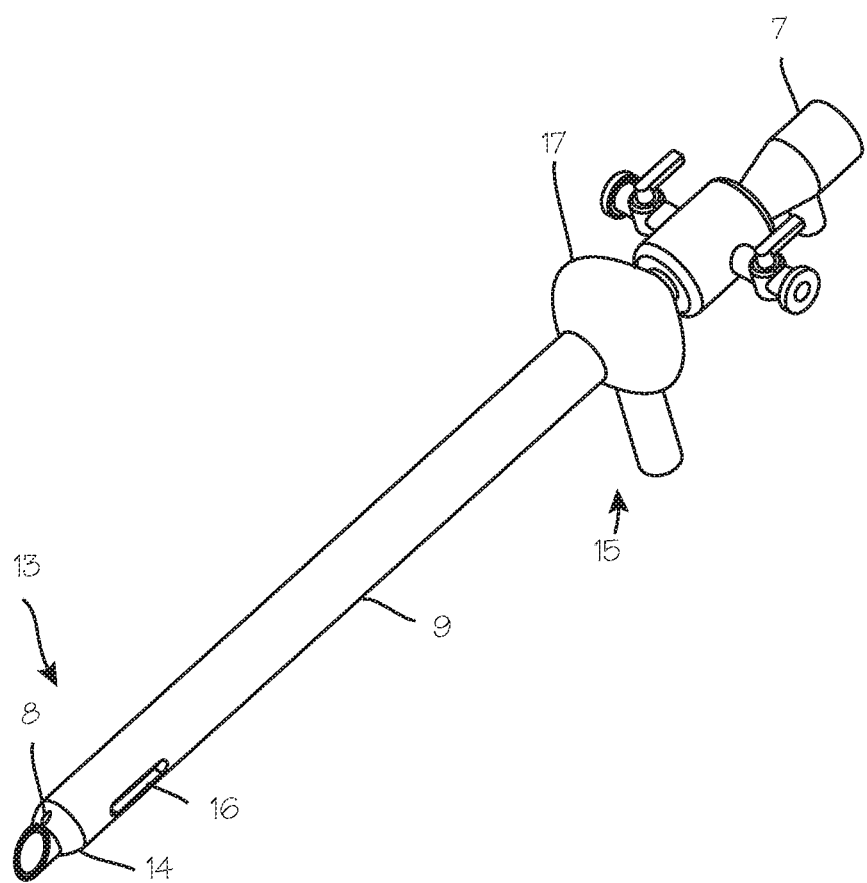
FIG. 2 illustrates the inflow/outflow sheath of the temperature control with an arthroscopic instrument disposed within the sheath.

FIG. 2 illustrates the inflow/outflow sheath of the temperature control having an arthroscopic instrument such as an arthroscope disposed within the sheath. Arthroscopic instruments can also include energy delivery devices such as ablation devices, arthroscopes, endoscopes, awls, picks, shavers, etc. The inflow/outflow sheath is a tube of resilient material, such as a sterilizable polymer like soft plastic or rubber, characterized by a central lumen. The inner diameter of the atraumatic sheath is sized and dimensioned to closely fit over the outer diameter of an arthroscopic instrument. The tube is characterized by a distal section 13 having a distal tip 14 and a proximal section 15. The distal tip 14 of the sheath 9 is provided with a beveled or rounded shape and an opening that is slightly smaller in diameter than the outer diameter of the distal tip of the arthroscope. The distal section of the sheath further comprises holes or other fluid apertures 16 placed in fluid communication with a fluid source or vacuum source. The proximal section 15 of the atraumatic sheath is provided with a hub 17 manufactured from an elastomer to allow medical personnel to easily pull the atraumatic sheath over and secure the sheath to the ablation device, rigid cannula, and/or arthroscopic instrument. The hub 17 is adapted for coupling to a fluid source and/or a vacuum source.

Holes 16 are provided in the outer wall of the distal section 13 of the sheath. The holes communicate with one or more inflow or outflow lumens in the sheath. The lumen or lumens communicate with a vacuum source, fluid source, therapeutic agent source or a combination of sources. Thus, the holes provide for the inflow and outflow of fluids to a surgical site during a procedure.

When the temperature control system 2 is in use, a user inserts the arthroscope or other arthroscopic instrument into the sheath. The distal tip expands as the distal end of the arthroscope slides past the distal tip of the sheath. Because the inner diameter of the tip is less than the outer diameter of the ablation device, the tip will form a seal fluid resistant seal with the outer surface of the ablation device.

A temperature sensor 8, such as a thermocouple, is disposed on the distal section 13 of the sheath 9. During surgery, the temperature sensor is placed in thermal communication with the fluid within the surgical site. Other devices for measuring temperature may be used as a temperature sensor 8 including thermistors, fiberoptics or other devices capable of measuring temperature. Alternatively, the temperature of the surgical site can be determined by measuring the temperature of the outflow fluid from the surgical site. The fluid being evacuated from a surgical site through the arthroscopic sheath (the outflow fluid) may be monitored using a temperature sensor placed in fluid communication with the outflow fluid to determine the temperature within the surgical site.

Figure 3:
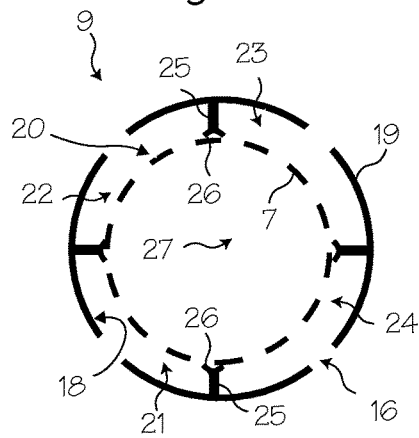
FIG. 3 illustrates a cross-sectional view of the inflow/outflow sheath in the temperature control system.
Figure 6:
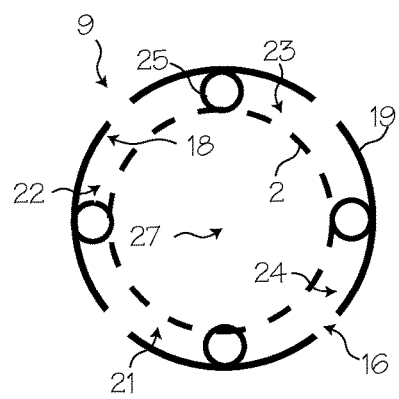
FIG. 6 illustrates a cross-sectional view of the inflow/outflow sheath in the temperature control system.
Figure 4:
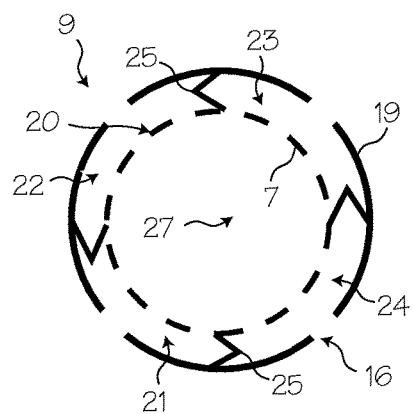
FIG. 4 illustrates a cross-sectional view of the inflow/outflow sheath in the temperature control system.
Figure 7:
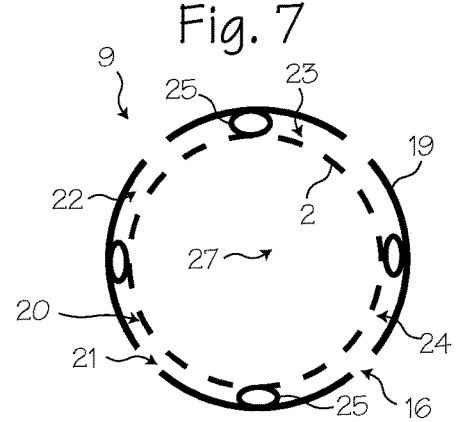
FIG. 7 illustrates a cross-sectional view of the inflow/outflow sheath in the temperature control system.
Figure 5:
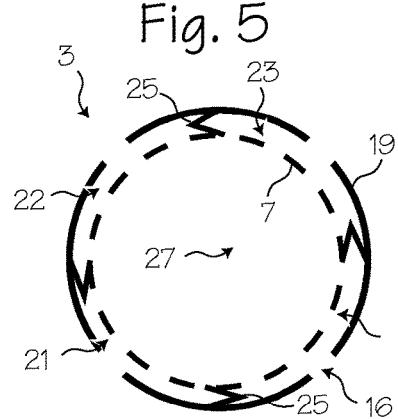
FIG. 5 illustrates a cross-sectional view of the inflow/outflow sheath in the temperature control system.
Figure 8:
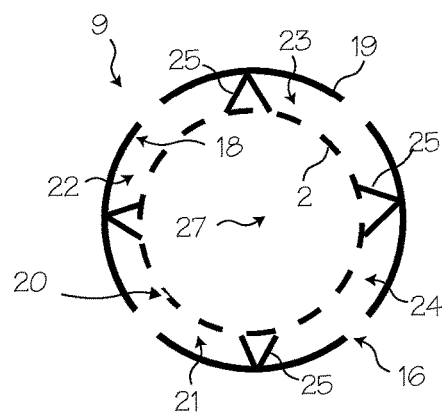
FIG. 8 illustrates a cross-sectional view of the inflow/outflow sheath in the temperature control system.

FIGS. 3 through 8 illustrate cross-sectional views of various configurations of the inflow/outflow sheath 9 in the temperature control system. FIG. 3 shows a cross-sectional view of the inflow/outflow sheath using the inner surface 18 of the outer wall 19 of the tube with the outer surface 20 of the ablation instrument to form inflow and outflow outer lumens 21, 22, 23 and 24. An inflow lumen allows fluid from a fluid source to flow into a surgical site while an out flow lumen allows fluid to be evacuated from a surgical site. Relatively stiff ribs 25 extending radially from the inner surface of the outer wall and running longitudinally along the sheath form a seal with the outer surface of the ablation device, thereby creating the four outer lumens. The ends of the ribs may be provided with elastic flanges 26 or extensions to enhance the seal made between the ribs and the ablation device. This configuration reduces the overall size of the combined inflow/outflow sheath and ablation device.

As depicted in FIG. 3, the arthroscope 7 is inserted into the sheath 9 through the central lumen 27. The ablation device 7 may or may not be covered by a secondary protective sheath prior to insertion. Once inserted, the outer surface of the ablation device 7 comes in contact with the flanges or extensions of the ribs. A raised distinct tract, also referred to as a land, may be used to contact the outer surface of the ablation device when the ribs do not have flanges or extensions. The force of the outer surface of the ablation device pushing against the ribs 25 and the rib flanges or rib extensions forms a seal between the ribs and the outer surface of the ablation device 7. Outer lumens 21, 22, 23 and 24 are created by the ribs 25, the outer surface of the ablation device 20, and inner surface 18 of the outer wall of the inflow/outflow sheath 9. The ribs 25 act as longitudinal struts that prevent the sheath 9 from collapsing as they support the sheath under compression. The ribs 25 reduce the unsupported span of the thin outer wall 19 in the traverse axis, further preventing the collapse of the sheath. The seals formed by the contact between the ribs and the outer surface of the ablation device prevent fluids from flowing between the outer lumens. The outer lumens 21, 22, 23 and 24 facilitate the substantially continuous inflow and outflow of fluids to and from a surgical site through the holes in the sheath. Check valves or gates may also be coupled to the inner surface of the inflow/outflow sheath within the outer lumens to prevent outflow fluids from flowing back towards the surgical site and to prevent inflow fluids from flowing out the proximal end of the sheath. Fluid can be introduced to the surgical site through the inflow/outflow sheath using an arthroscopy pump or by gravity feed. Furthermore, fluid is evacuated from a surgical site through the inflow/outflow sheath using a vacuum source, siphon or gravity.

Figure 9:
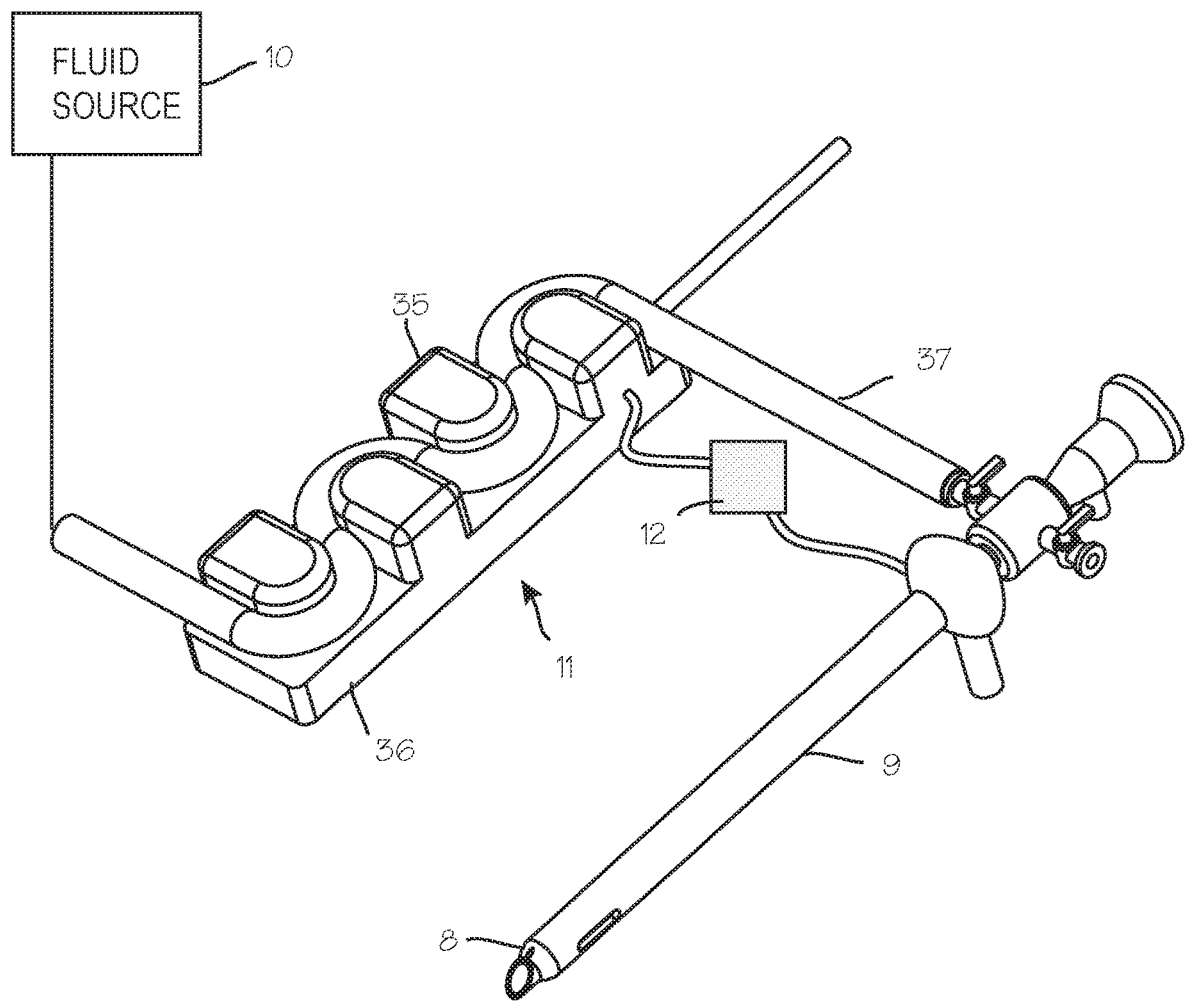
FIG. 9 illustrates the chilling module in detail.

The chilling module 11 is illustrated in detail in FIG. 9. The chilling module is a device capable of lowering the temperature of fluid prior to entering the surgical site. During surgical procedures requiring ablation, inflow fluid is cooled prior to entering the surgical site. The chilling module comprises one or more heat sinks 35, a thermoelectric or Peltier cooler 36 having a fan, and a control system 12.

As shown in FIG. 9, a fluid inflow 37 tube in fluid communication with the inflow/outflow sheath and a fluid source 10 is interwoven between one or more heat sinks 35. The Peltier cooler 36 is placed in thermal communication with the heat sinks 35. The control system 12 is in electrical communication with the Peltier module 36 and the temperature sensor 8 is disposed on the distal section of the sheath. Using the thermocouple, the control system 12 monitors the temperature of the surgical site. When the temperature exceeds safe levels, such as exceeding 113° C., the control system instructs the Peltier module automatically, without user intervention, to cool the inflow fluid. The inflow fluid is cooled to a temperature sufficient to reduce the temperature within the surgical site to a safe level in order to prevent tissue damage. When the temperature in the surgical site reaches a safe level (a temperature level that does not have the potential to cause damage to surrounding tissue) the control system instructs the cooling module automatically to reduce or cease lowering the temperature of the inflow fluid. A user can also use the control system directly to control the temperature level of the inflow fluid with a user interface operably coupled to the control system. A temperature sensor reader and display can also be placed in electrical communication with the temperature sensor and the control system. The reader is provided with an LCD and is capable of displaying the temperature taken by the temperature sensor, warnings, graphical depictions and data.

Figure 10A:
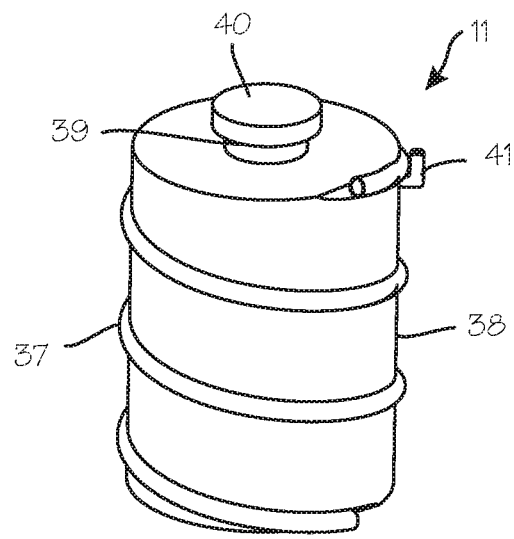
FIG. 10A illustrates a chilling module comprising a canister of refrigerant.
Figure 10B:
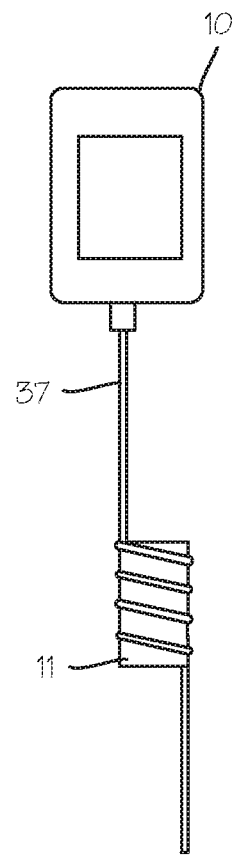
FIG. 10B illustrates a chilling module comprising a canister of refrigerant.

The chilling module 11 can comprise other devices suitable for manipulating the temperature of inflow fluid prior to entering the surgical site including heat sinks, refrigerators, heat exchangers, chemical and non-chemical ice packs, and refrigerants. The chilling module 11 may be a separate device in-line with an arthroscopic pump or built into an arthroscopic pump operating in line with a fluid delivery system. FIGS. 10A and 10B illustrate a chilling module 11 comprising a canister of refrigerant. Here, the chilling module 11 comprises a canister 38 having an input aperture 39 and a removable lid 40. The canister is filled with ice, refrigerated gel or other refrigerant through the input aperture. The inflow tube 37 is disposed about the exterior of the canister and removably coupled to the canister using a retention tab 41. The inflow tube is placed in thermal communication with the canister. When inflow fluid from a fluid source passes through the inflow tube as illustrated in FIG. 10B, the temperature of the inflow fluid is reduced prior to entering a surgical site by the refrigerant within the canister.

Figure 11:
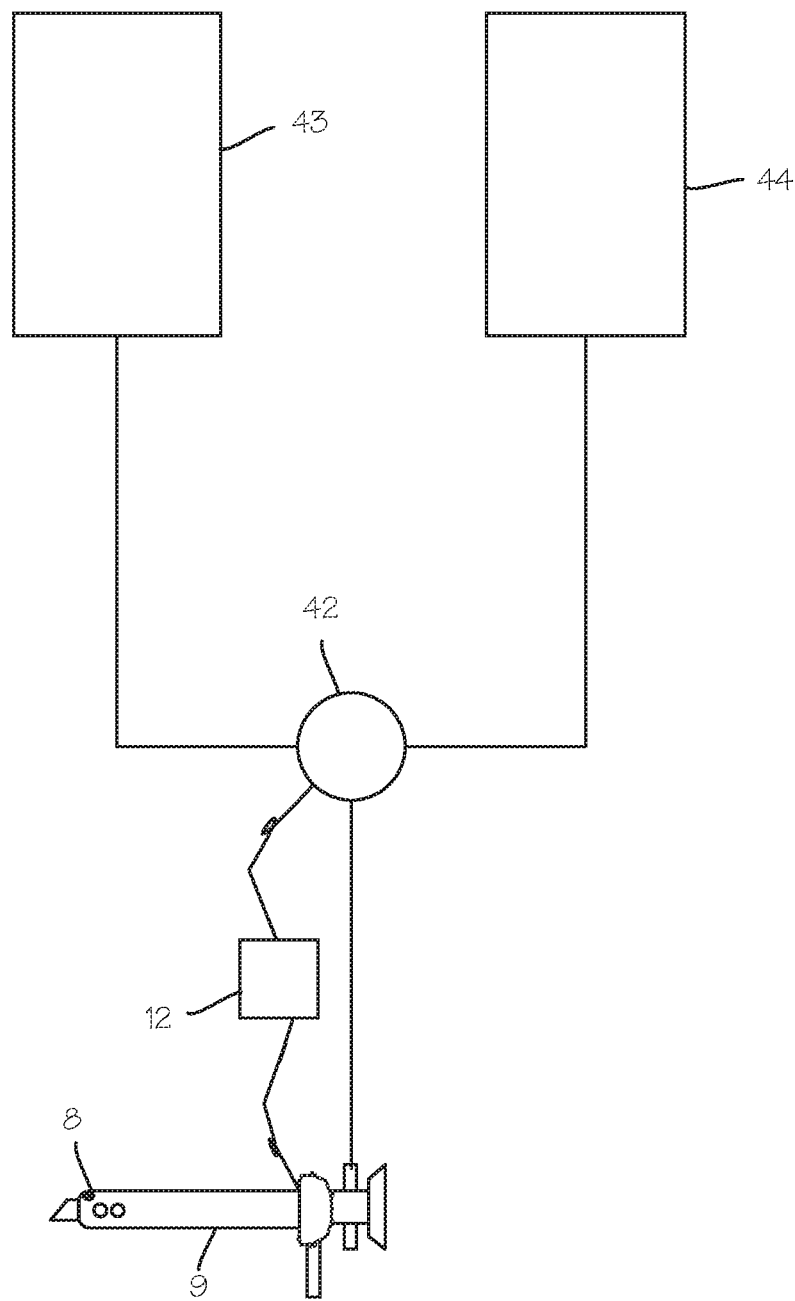
FIG. 11 shows a temperature control system with a mixing valve.

FIG. 11 shows an alternative configuration of the temperature control system 2 and method of cooling or heating the inflow fluid. Here, a mixing valve 42 is placed in fluid communication with a first fluid source 43 having warm irrigation fluid, a second fluid source 44 having cool irrigation fluid and the inflow/outflow sheath 9. The control system 12 is placed in electrical communication with the temperature sensor 8 disposed on the sheath and the mixing valve 42. During surgical procedures, the temperature sensor 8 takes temperature measurements from the surgical site. The control system 12 instructs the valve 42 to mix fluid from the first fluid source 43 and the second fluid source 44 to obtain an appropriate temperature for the inflow fluid to maintain the surgical site temperature at a safe level.

Figure 12:
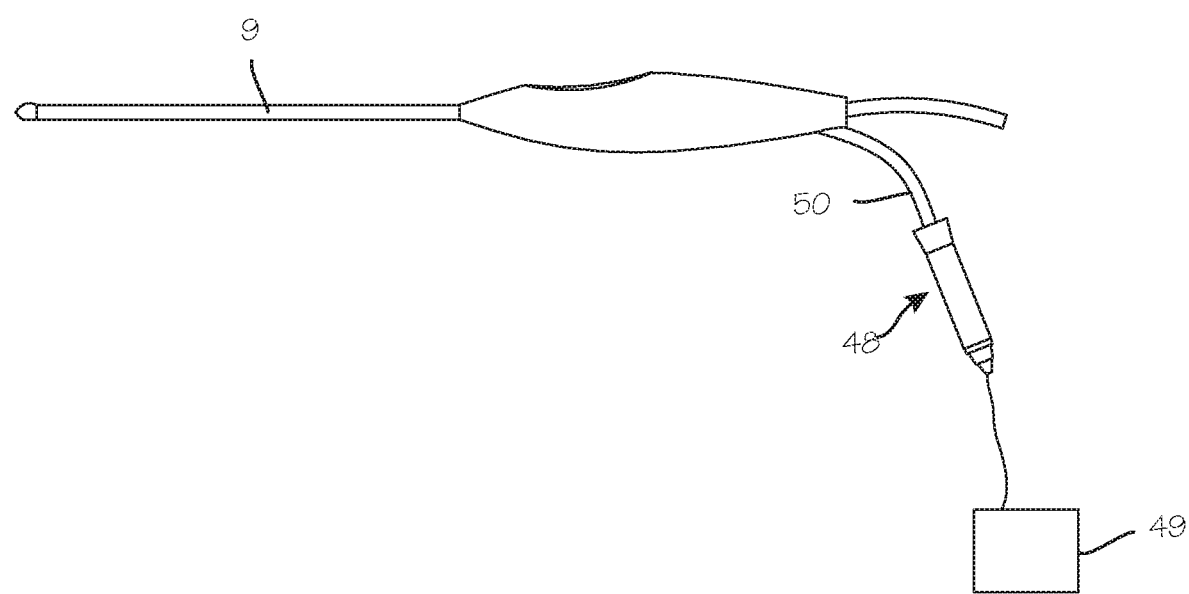
FIG. 12 illustrates the temperature control system having an in-line temperature-warning device.

As shown in FIG. 12, in-line temperature-warning devices 48 may be incorporate in the temperature control system 2. Fluid is evacuated from the surgical site through the inflow/outflow sheath 9 to a vacuum source 49 with a fluid outflow tube 50. Temperature-warning devices having in-line temperature sensors may be placed in thermal communication with the outflow fluid. This is accomplished by placing the sensors in fluid communication with the outflow fluid or by placing the sensors in contact with the outflow tube. The sensors are operably coupled to warning devices that provide visual, audible or visual and audible warnings when temperatures exceed a safe threshold. The temperature-warning devices can be provided as an integral part of the outflow tube or as temperature warning collars that provide visual, audible or visual and audible warnings when temperatures exceed a safe threshold.

Figure 13A:
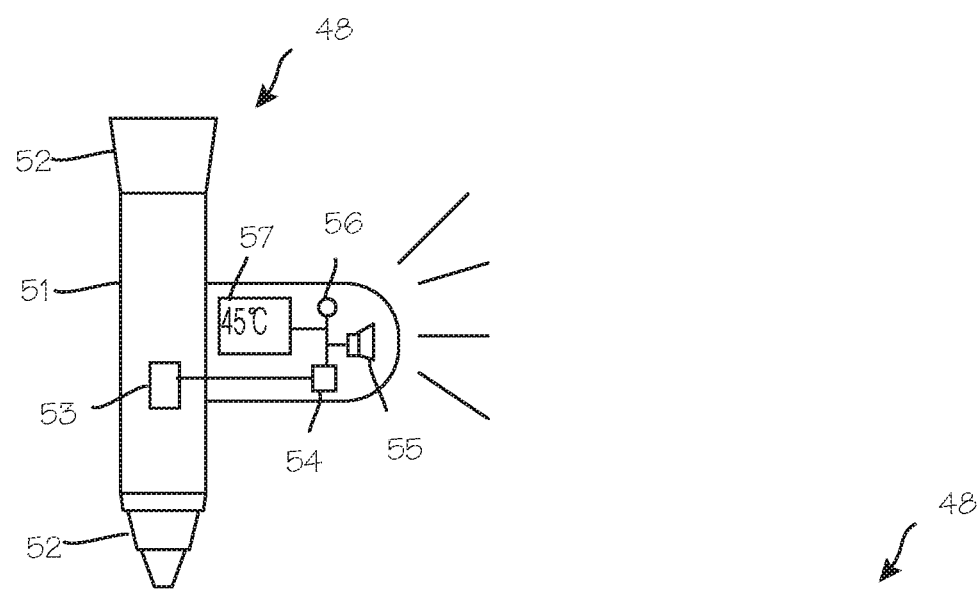
FIG. 13A depicts a temperature-warning device.

FIG. 13A depicts a temperature-warning device. The temperature-warning device comprises a collar 51 of polymeric material having an inner diameter sized and dimensioned to slip fit over a fluid outflow tube from a surgical site. The collar 51 may also be provided with fittings 52 capable of operably coupling the collar to the outflow tube and fluid source. The temperature-warning device further comprises a temperature sensor 53 such as a thermocouple that can be placed in thermal communication with outflow fluid through contact with the wall of the outflow tube or by being placed in fluid communication with the outflow fluid. The temperature-warning device provides audible warnings of dangerous temperature within a surgical site to users by placing the thermocouple in electrical communication with a control integrated circuit board 54, a piezoelectric buzzer 55 and a power source 56 disposed within the collar. A digital display 57 may also be provided capable of displaying the temperature and visual warnings. The control board is able to monitor the temperature of the outflow fluid using the thermocouple and activate the piezoelectric buzzer when the temperature of the outflow fluid exceeds a safe threshold.

Figure 13B:
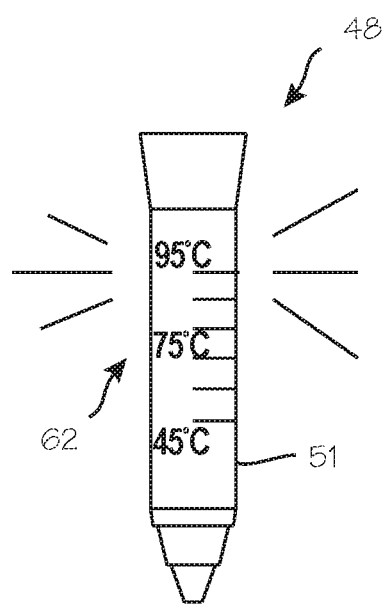
FIG. 13B depicts a temperature-warning device.

In an alternative configuration of the temperature-warning device shown in FIG. 13B, a collar 51 of polymeric material having an inner diameter sized and dimensions to slip fit over a fluid outflow tube is provided with a visual temperature indicator 62 such as a thermochromic liquid crystal thermometer. Thermochromic Liquid Crystals (TLC's) are highly sensitive materials that respond to temperature. Liquid crystals can change from black to a rainbow of colors upon heating and then back to black again upon cooling. Furthermore, liquid crystals can be formulated into thermometers with a wide or a narrow temperature sensitivity and can be made into any size or shape. The thermometer disposed within the collar can be placed in thermal communication with the outflow fluid by fluid communication with the outflow fluid flowing through the collar. Alternatively, the thermometer can be placed in thermal communication with the outflow fluid through the wall of the outflow tube disposed within the collar. The thermochromic liquid crystal thermometer in the collar provides a visual indicator to a user by changing colors when the temperature of the outflow fluid exceeds a threshold that indicates the fluid temperature within the joint is approaching 113° F.

When in use during arthroscopic shoulder surgery, an arthroscope device is inserted through the central lumen of the sheath in the temperature control device. The arthroscope with the sheath is then introduced through a first portal to visualize the surgical site. The surgeon introduces the ablation device into the shoulder via a second portal. The ablation device is used to smooth surfaces and seal fissures in articular cartilage. The sheath provides fluid inflow and outflow to the surgical site. The surgeon will activate the radio frequency ablation device during surgery generating heat within the surgical site. The temperature sensor disposed on the distal end of the sheath senses the temperature of the fluid within the surgical site. When the temperature exceeds a safe threshold, such as a temperature exceeding 108° F., the control system in electrical communication with the temperature sensor and the chilling module instructs the chilling module to cool down the inflow fluid. The lower temperature inflow fluid is introduced to the surgical site and reduces the temperature at the surgical site to a safe level (below 113° F.) that does not cause damage to surrounding tissue. Once acceptable temperature levels have been reached, the chilling module can be used to maintain the temperature level at the surgical site by cooling the inflow fluid when necessary. During arthroscopic surgery, it is important for surgeons to complete the surgery in a timely manner to avoid fluid extravasation, reduce the chance of infection, minimize complications and reduce medical costs.

While the preferred embodiments of the devices and methods have been described in reference to the environment in which they were developed, they are merely illustrative of the principles of the inventions. Other embodiments and configurations may be devised without departing from the spirit of the inventions and the scope of the appended claims.

I claim:

1. A system for use in arthroscopic surgery comprising:
    a sheath characterized by a central lumen, a distal section and a proximal end wherein the central lumen is sized and dimensioned to receive an arthroscopic instrument, said sheath further comprising an inflow lumen and an outflow lumen;
    a temperature sensor disposed on the distal section of the sheath;
    a fluid source in fluid communication with the inflow lumen;

a chilling module in thermal communication with the fluid source; and a control system in electrical communication with the temperature sensor and the chilling module, said control system capable of obtaining a temperature reading from the temperature sensor and automatically operating the chilling module when the temperature reading exceeds 108° F. to introduce lower temperature inflow fluid to the surgical site to reduce the temperature at the surgical site to a level that does not cause damage to the surrounding tissue.

2. The system of claim 1 further comprising a vacuum source in fluid communication with the outflow lumen.

3. The system of claim 1 further comprising a fluid aperture disposed on the distal section of the sheath in fluid communication with the inflow lumen.

4. The system of claim 1 further comprising a fluid aperture in fluid communication with the outflow lumen.

5. The system of claim 1 further comprising a temperature-warning device in thermal communication with an outflow fluid from the outflow lumen.

6. The system of claim 5 wherein the temperature-warning device provides an audible warning when the temperature of the outflow fluid exceeds a safe threshold.

7. The system of claim 5 wherein the temperature-warning device provides a visual warning when temperature of an outflow fluid exceeds a safe threshold.

\* \* \* \* \*